US010485454B2

(12) United States Patent
Tas et al.

(10) Patent No.: US 10,485,454 B2
(45) Date of Patent: Nov. 26, 2019

(54) SYSTEMS AND METHODS FOR MARKERLESS TRACKING OF SUBJECTS

(71) Applicant: NEUROPATH SPRL, Louvain-la-Neuve (BE)

(72) Inventors: Benoit Yvonne Tas, Heverlee (BE); Eric Michael Clark, Burlington, VA (US)

(73) Assignee: NEUROPATH SPRL (BE)

(*) Notice: Subject to any disclaimer, the term of this patent is extended or adjusted under 35 U.S.C. 154(b) by 0 days.

(21) Appl. No.: 15/984,986

(22) Filed: May 21, 2018

(65) Prior Publication Data

US 2018/0338710 A1 Nov. 29, 2018

Related U.S. Application Data

(60) Provisional application No. 62/510,749, filed on May 24, 2017.

(51) Int. Cl.
*G06K 9/00* (2006.01)
*A61B 5/11* (2006.01)
(Continued)

(52) U.S. Cl.
CPC .......... *A61B 5/1128* (2013.01); *A61B 5/0035* (2013.01); *A61B 5/0075* (2013.01);
(Continued)

(58) Field of Classification Search
CPC .. A61B 5/1128; A61B 5/0035; H04N 13/204; G06K 9/00268
See application file for complete search history.

(56) References Cited

U.S. PATENT DOCUMENTS 6,816,603 B2 11/2004 David et al.
7,467,603 B2 12/2008 Davis
(Continued)

FOREIGN PATENT DOCUMENTS

AU 2015234210 B2 9/2015
CA 2934744 A1 9/2015
(Continued)

OTHER PUBLICATIONS

Goetz et al., "MDS-UPDRS," International Parkinson and Movement Disorder Society, 2008, 32 pages.
(Continued)

*Primary Examiner* — Gregory M Desire
(74) *Attorney, Agent, or Firm* — Dickinson Wright PLLC; Brian T. Mangum

(57) ABSTRACT

Markerless tracking systems and methods for markerless tracking of subjects. In one embodiment, the markerless tracking system includes an active 3D infrared camera, a memory, and an electronic processor. The electronic processor is configured to extract body motion data for a subject's body from depth data captured by the active 3D infrared camera. The electronic processor is also configured to detect movements of the subject's body using the body motion data. The electronic processor is further configured to determine attributes for the movements of the subject's body using the body motion data. The electronic processor is also configured to assign a rating by comparing the determined attributes with a plurality of benchmarks included in a pre-stored movement profile in the memory. The electronic processor is further configured to create a session record for the subject. The session record includes the body motion data, the determined attributes, and the assigned rating.

17 Claims, 9 Drawing Sheets

(51) Int. Cl.
*H04N 13/204* (2018.01)
*A61B 5/00* (2006.01)
*H04N 5/33* (2006.01)
*G16H 40/63* (2018.01)
*G16H 20/30* (2018.01)

(52) U.S. Cl.
CPC .......... *A61B 5/0077* (2013.01); *A61B 5/4082* (2013.01); *A61B 5/7246* (2013.01); *A61B 5/7278* (2013.01); *G06K 9/00268* (2013.01); *G06K 9/00342* (2013.01); *G16H 20/30* (2018.01); *G16H 40/63* (2018.01); *H04N 5/33* (2013.01); *H04N 13/204* (2018.05); *A61B 2576/00* (2013.01)

(56) References Cited

U.S. PATENT DOCUMENTS

| | | |
|---|---|---|
| 7,519,210 B2 | 4/2009 | Hirsch et al. |
| 7,693,315 B2 | 4/2010 | Krishnan et al. |
| 7,826,815 B2 | 11/2010 | Ajram et al. |
| 7,953,613 B2 | 5/2011 | Gizewski |
| 8,007,450 B2 | 8/2011 | Williams |
| 8,075,499 B2 | 12/2011 | Nathan et al. |
| 8,126,736 B2 | 2/2012 | Anderson et al. |
| 8,139,822 B2 | 3/2012 | Selner |
| 8,348,840 B2 | 1/2013 | Heit et al. |
| 8,676,293 B2 | 3/2014 | Breen et al. |
| 8,685,093 B2 | 4/2014 | Anderson et al. |
| 8,727,976 B2 | 5/2014 | Iliff |
| 8,740,819 B2 | 6/2014 | Davis et al. |
| 8,777,878 B2 | 7/2014 | Deitz |
| 8,821,416 B2 | 9/2014 | Johansson et al. |
| 9,129,054 B2 | 9/2015 | Nawana et al. |
| 9,223,837 B2 | 12/2015 | Djugash |
| 9,232,912 B2 | 1/2016 | McQueen et al. |
| 9,235,977 B2 * | 1/2016 | Deutsch ............... G08B 21/245 |
| 9,622,686 B1 * | 4/2017 | Berme ................... A61B 5/112 |
| 9,696,387 B2 * | 7/2017 | Pesola ................... A61N 2/006 |
| 2010/0191100 A1 | 7/2010 | Anderson et al. |
| 2010/0222711 A1 | 9/2010 | Lajeunesse |
| 2011/0066068 A1 | 3/2011 | Duffy |
| 2012/0214594 A1 | 8/2012 | Kirovski et al. |
| 2012/0259648 A1 | 10/2012 | Mallon et al. |
| 2013/0190135 A1 | 7/2013 | Pryor |
| 2013/0281798 A1 | 10/2013 | Rau et al. |
| 2013/0281888 A1 | 10/2013 | Bender et al. |
| 2013/0324857 A1 | 12/2013 | Kurillo et al. |
| 2013/0324868 A1 | 12/2013 | Kaib et al. |
| 2014/0058189 A1 * | 2/2014 | Stubbeman ............ A61N 2/002 600/13 |
| 2014/0139616 A1 | 5/2014 | Pinter et al. |
| 2014/0147820 A1 | 5/2014 | Snow et al. |
| 2014/0153794 A1 | 6/2014 | Varaklis et al. |
| 2014/0172460 A1 | 6/2014 | Kohli |
| 2014/0176130 A1 | 6/2014 | Bueno Palacios |
| 2014/0228985 A1 | 8/2014 | Elliott et al. |
| 2014/0316242 A1 | 10/2014 | Musahl et al. |
| 2015/0092998 A1 | 4/2015 | Liu et al. |
| 2015/0157274 A1 | 6/2015 | Ghassemzadeh et al. |
| 2015/0272511 A1 | 10/2015 | Najafi et al. |
| 2015/0306340 A1 | 10/2015 | Giap et al. |
| 2015/0332004 A1 | 11/2015 | Najafi et al. |
| 2016/0022193 A1 | 1/2016 | Rau et al. |
| 2016/0073614 A1 | 3/2016 | Lampe et al. |
| 2017/0112418 A1 | 4/2017 | Comeau et al. |
| 2017/0287146 A1 * | 10/2017 | Pathak .................... G06T 7/251 |
| 2019/0042832 A1 * | 2/2019 | Venshtain ............. H04N 7/157 |

FOREIGN PATENT DOCUMENTS

| | | |
|---|---|---|
| CA | 2934744 C | 11/2016 |
| CN | 106456057 A | 2/2017 |
| WO | 2015/139145 A1 | 9/2015 |

OTHER PUBLICATIONS

Knippenberg et al., "Markerless motion captures systems as training device in neurological device in neurological rehabilitation: a systematic review of their use, application, target population and efficacy," Journal of NeuroEngineering and Rehabilitation, 2017, 14:61, 11 pages.
Occipital, "Simple, precise 3D scanning for orthotics and prosthetics," <https://structure.io/use/orthotics-prosthetics> webpage available since Sep. 18, 2016.
Sword Health, <https://www.swordhealth.com/> webpage available since Nov. 23, 2014.
Tomkins, "Kinect-like Occipital Structure Sensor lets your iPad model the world in 3D," <https://www.imaging-resource.com/news/2013/09/25/kinect-like-occipital-structure-sensor-lets-your-ipad-model-the-world-in-3d> Sep. 25, 2013.
Xsens <https://www.xsens.com/> webpage available since Feb. 25, 2001.
Agrawal et al., "Assessment of motion of a swing leg and gait rehabilitation with a gravity balancing exoskeleton," IEEE Transactions on Neural Systems and Rehabilitation Engineering, 2007, 15(3): 410-420.
Ahlrichs et al., "Parkinson's Disease Motor Symptoms in Machine Learning: a review," Health Informatics—An International Journal (HIIJ), 2013, 2(4): 18 pages.
Andrikula et al., "2D human pose estimation: New benchmark and state of the art analysis," CVPR, 2014, 8 pages.
Bassily et al., "Intuitive and adaptive robotic arm manipulation using the leap motion controller," 41st International Symposium on Robotics, 2014, 78-84.
Bind et al., "A Survey of Machine Learning Based Approaches for Parkinson Disease Prediction," International Journal Computer Science and Information Technologies, 2015, 6(2): 1648-1655.
Brokaw, "Hand Spring Operated Movement Enhancer (HandSome): A Portable Passive Hand Exoskeleton for Stroke Rehabilitation," IEEE Transactions on Neural Systems and Rehabilitation Engineering, 2011, 19(4): 391-399.
Butt et al., "Leap motion evaluation for assessment of upper limb motor skills in Parkinson's disease," International Conference on Rehabilitation Robotics, Jul. 2017, 116-121.
Caliskan et al., "Diagnosis of the Parkinson Disease by Using Deep Neural Network Classifier," IU-JEEE, 2017, 17(2): 3311-3318.
Cellan-Jones, "Parkinson's diagnosis set to be sped up by Tencent's AI," <https://www.bbc.com/news/technology-45760649> Oct. 8, 2018.
Ceseracciu et al., "Comparison of Markerless and Marker-Based Motion Capture Technologies through Simultaneous Data Collection during Gait: Proof of Concept," PLOS One, 2014, 9(3): e87640, 7 pages.
Cho et al., "A vision-based analysis system for gait recognition in patients with Parkinson's disease," Expert Systems with Applications, 2009, 36(2009): 7033-7039.
CloudUPDRS <http://www.updrs.net/> webpage available as early as Apr. 8, 2017.
Das et al., "Quantitative Measurement of Motor Symptoms in Parkinson's Disease: A Study with Full-body Motion Capture Data," Annual International Conference of the IEEE Engineering in Medicine and Biology Society, 2011, 4 pages.
Dror et al., "Automatic Assessment of Parkinson's Disease From Natural Hands Movements Using 3D Depth Sensor," IEEE 28th Convention of Electrical and Electronics Engineers in Israel, 2014, 5 pages.
Eskofier et al., "Recent machine learning advancements in sensor-based mobility analysis: Deep learning for Parkinson's disease assessment," IEEE Engineering in Medicine and Biology Society, 2016, 4 pages.
Esser et al., "Validity and inter-rater reliability of inertial gait measurements in Parkinson's disease: A pilot study," Journal of Neuroscience Methods, Jan. 2012, 205(2012): 177-181.
Galna et al., "Accuracy of the Microsoft Kinect sensor for measuring movement in people with Parkinson's disease," Gait & Posture, 2014, 39(2014): 1062-1068.

(56) References Cited

OTHER PUBLICATIONS

Galna et al., "Retraining function in people with Parkinson's disease using the Microsoft Kinect: game design and pilot testing," Journal of Neuroengineering and rehabilitation, 2014, 11:60, 12 pages.
Goetz et al., "Movement disorder society-sponsored revision of the unified Parkinson's disease rating scale (MDS-UPDRS): scale presentation and clinimetric testing results," Movement Disorders, 2008, 22(1): 41-47.
Green et al., "Video analysis of gait for diagnosing movement disorders," Journal of Electronic Imaging, 2000, 9(1): 16-21.
Grover et al., "Predicting Severity of Parkinson's Disease Using Deep Learning," Procedia Computer Science, 2018, 132(2018): 1788-1794.
Grubisic et al., "Novel approaches in hand rehabilitation," Periodicum Biologorum, Apr. 2015, 117(1): 139-145.
Hammerla et al., "PD Disease State Assessment in Naturalistic Environments Using Deep Learning," AAAI Conference on Artificial Intelligence, 2015, 1742-1748.
Hoehn et al., "Parkinsonism: onset, progression, and mortality," Neurology, 1967, 17(5): 427-442.
Hondori et al., "A Review on Technical and Clinical impact of Microsoft Kinect on Physical Therapy and Rehabilitation," Hindawi Journal of Medical Engineering, 2014, 16 pages.
InFlect Flex Sensor, <https://www.brewerscience.com/products/inflect-flex-sensor/?_vsrefdom=adwords&gclid=EAlalQobChMl08qBvvbQ3glVRrvtCh1VxA_TEAAYASAAEgKOnvD_BwE>.
International Parkinson and Movement Disorder Society (MDS), "Unified Dyskinesia Rating Scale (UDysRS)," https://www.movementdisorders.org/MDS-Files1/PDFs/UDysRS_English_FINAL.pdf, 2008, accessed Nov. 12, 2018.
International Search Report and Written Opinion for Application No. PCT/US2018/033715 dated Oct. 19, 2018 (17 pages).
Jiting et al., "Development of a Hand Exoskeleton System for Index Finger Rehabilitation," Chinese Journal of Mechanical Engineering, 2011, 25(2): 223-233.
Kaia <https://www.kaia-health.com/?locale=en> webpage available as early as Jan. 22, 2019.
Khademi et al., "An assistive tabletop keyboard for stroke rehabilitation," ACM International Conference on Interactive Tabletops and Surfaces, 2013, 337-340.
Khan et al., "A computer vision framework for finger-tapping evaluation in Parkinson's disease," Artificial Intelligence in Medicine, 2014, 60(2014): 27-40.
Kim et al., "Automatic estimation of Parkinson's disease severity from diverse speech tasks," Proceedings of Interspeech, Sep. 2015, 5 pages.
Kinetisense <https://kinetisense.com/> webpage available as early as May 3, 2014.
Knippenberg et al., "Markerless motion capture systems as training device in neurological rehabilitation: a systematic review of their use, application, target population and efficacy," Journal of NeuroEngineering and Rehabilitation, 2017, 14:61, 11 pages.
Lee et al., "Video Analysis of Human Gait and Posture to Determine Neurological Disorders," EURASIP Journal Image and Video Processing, 2008, 12 pages.
Li et al., "Vision-Based Assessment of Parkinsonism and Levodopa-Induced Dyskinesia with Deep Learning Pose Estimation," arXiv:1707.09416v2, 2017, 8 pages.
Loh et al., "Fifty Years of Classification and Regression Trees," International Statistical Review, 2014, 82(3): 329-348.
MachineMedicine <https://machinemedicine.com/> webpage avilable as early as May 15, 2010.
MARSystems <http://www.mar-systems.co.uk/> webpage available as early as Mar. 3, 2006.
Martinez et al., "Accuracy of Markerless 3D Motion Capture Evaluation to differentiate between on/off status in Parkinson's disease after deep brain simulation," Hindawi Parkinson's Disease Journal, 2018, 7 pages.

Mullin, "Pfizer and IBM Launch Ambitious 'Internet of Things' for Parkinson's Research," Forbes, Apr. 7, 2016 <http://blogs.forbes.com/emilymullin/?p=721>.
Nussbaum et al., "Alzheimer's disease and Parkinson's disease," The New England Journal of Medicine, 2003, 348: 1356-1364.
Otte et al., "Accuracy and Reliability of the Kinect Version 2 for Clinical Measurement of Motor Function," PLOS One, 2016, 11(11): e0166532, 17 pages.
Pachoulakis et al., "Building a Gait Analysis Framework for Parkinson's Disease Patients: Motion Capture and Skeleton 3D Representation," International Conference on Telecommunications and Multimedia, 2014, 7 pages.
Passadiki et al., "Decomposition of complex movements into primitives for Parkinson's disease assessment," IBM J. Res. & Dev., 2018, 62(1): paper 5, 11 pages.
Pedrosa et al., "Machine Learning Application to Quantify the Tremor Level for Parkinson's Disease Patients," Procedia Computer Science, 2018, 6 pages.
Pintea et al., "Hand-tremor frequency estimation in videos," arXiv:1809.03218v1, Sep. 2018, 16 pages.
Rao et al., "Validating an objective video-based dyskinesia severity score in Parkinson's disease patients," Parkinsonism and Related Disorders, 2013, 19(2013): 232-237.
Rigas et al., "Real-Time Quantification of Resting Tremor in the Parkinson's Disease," 31st Annual International Conference of the IEEE EMBS, 2009, 1306-1309.
Shotton et al., "Real-time human pose recognition in parts from single depth images," CVPR, 2011, 8 pages.
Silva de Lima et al., "Feasibility of large-scale deployment of multiple wearable sensors in Parkinson's disease," PLOS one, 2017, 12(12): 0189161, 15 pages.
Stone et al., "Patient non-compliance with paper and electronic diaries," controlled Clinical Trials, 2003, 324, 1193-1194.
Sucar et al., "Gesture therapy: a vision-based system for arm rehabilitation after stroke," Biomedical Engineering Systems and Technologies, Springer, 2009, 5 pages.
The Center for Quality Assessment and Improvement in Mental Health, "Abnormal Involuntary Movement Scale (AIMS)—Overview," http://www.cqaimh.org/pdf/tool_aims.pdf, accessed Nov. 12, 2018.
Ushaw et al., "Benchmarking Motion Sensing Devices for Rehabilitative Gaming," ACM, Apr. 2015, 5 pages.
Wei et al., "Convolutional Pose Machines," arXiv:1602.00134v4, Apr. 2016, 9 pages.
Wikipedia, "Sensitivity and specificty," <https://en.wikipedia.org/wiki/Sensitivity_and_specificity> webpage as early as Sep. 13, 2006.
Zhang et al., "Can a Smartphone Diagnose Parkinson Disease? A Deep Neural Network Method and Telediagnosis System Implementation," Hindawi Parkinson's Disease Journal, 2017, 11 pages.
Duda et al., "Pattern classification and scene analysis," John Wiley & Sons, New York, 1973.
Gupta et al., "Pathological speech processing: state-of-the-art, current challenges, and future directions," IEEE 2016.
Kao et al., "Validation of Automated Mobility Assessment using a Single 3d Sensor," conference paper from Human Interaction Prediction Using Deep Temporal Features, 2016.
Khademi et al., "Free-hand interaction with leap motion controller for stroke rehabilitation," 32nd Annual ACM Conference on Human Factors in Computing Systems, 2014.
Rocha et al., "Kinect v2 Based System for Parkinson's Disease Assessment," IEEE EMBS, 2015.
Sanchez et al., "A pneumatic robot for re-training arm movement after stroke: Rationale and mechanical design," Proceedings of the 9th International Conference on Rehabilitation Robotics, vol. 15, Jul. 2005.
Zhan et al., "Using Smartphones and Machine Learning to Quantify Parkinson Disease Severity: The Mobile Parkinson Disease Score," JAMA Neurology brief report, 2018.

\* cited by examiner

SYSTEMS AND METHODS FOR MARKERLESS TRACKING OF SUBJECTS

RELATED APPLICATIONS

This application claims priority to U.S. Provisional Application No. 62/510,749, entitled "METHODS AND SYSTEM FOR ASSESSING NEUROLOGICAL DISEASE," filed May 24, 2017, the entire contents of which is incorporated herein by reference.

BACKGROUND

Parkinson's disease affects between 5 and 7 million people, and is the second largest neurological disease. Parkinson's disease is degenerative and there is currently no cure. Parkinson's disease is caused by a loss of dopamine in the neurons of the human body. To track the progression of the disease, subjects are periodically evaluated by medical professionals using established rating scales. An example rating scale for Parkinson's disease is the Movement Disorder Society unified Parkinson's disease rating scale (MDS-UPDRS). As explained below, the current examination methods for subjects with Parkinson's disease (and other neurological diseases) have several significant limitations.

Currently, examinations of subjects are performed by doctors during office visits. Subjects with Parkinson's disease typically visit a doctor's office once or twice a year. Thus, their condition is only monitored 1 to 2 hours per year. This leaves about 8,758 hours per year when their condition is not being monitored.

Established rating scales (such as the MDS-UPDRS) typically include questionnaires and a series of motor exercises. Currently, a doctor watches a subject performing each of the motor exercises and then determines a rating for the subject's movement based on a series of prescribed guidelines. Many of the prescribed guidelines are subjective and open to the interpretation of the doctor performing the examination. For example, a prescribed guideline may require the doctor to differentiate between a subject walking with minor gait impairment and with substantial gait impairment. In addition, many of the prescribed guidelines require the doctor to evaluate attributes that are difficult to discern with eyeball judgement. For example, a prescribed guideline may require the doctor to differentiate a hand tremor between 1 centimeter and 3 centimeters from a hand tremor between 3 centimeters and 5 centimeters.

Further, Parkinson's disease is a very individual disease. Every subject develops different motor and non-motors symptoms at different rates. The currently examination methods employ fixed rating scales that do not account for the symptom development of individual subjects.

SUMMARY

The disclosure provides a system for markerless tracking of a subject performing a motor exercise. In one embodiment, the system includes an active 3D infrared camera, a memory, and an electronic processor. The active 3D infrared camera captures depth data of a body of the subject during the motor exercise. A movement profile is pre-stored in the memory. The movement profile includes a plurality of benchmarks. The electronic processor is configured to extract body motion data for the subject's body from the captured depth data. The body motion data includes a set of 3D coordinates for a plurality of body joints for each frame of the captured depth data. The electronic processor is also configured to detect movements of the subject's body using the body motion data. The electronic processor is further configured to determine a set of attributes for the detected movements of the subject's body using the body motion data. The electronic processor is also configured to assign a rating for the motor exercise by comparing the set of attributes for the detected movements of the subject's body with the plurality of benchmarks included in the pre-stored movement profile. The electronic processor is further configured to create a session record for the subject. The session record includes the body motion data, the set of attributes for the detected movements of the subject's body, and the assigned rating for the motor exercise.

The disclosure also provides a system for markerless tracking of subjects located in a space. In one embodiment, the system includes an active 3D infrared camera and an electronic processor. The active 3D infrared camera captures depth data of the space. The electronic controller is configured to extract body motion data for a body of a first subject located in the space from the captured depth data. The body motion data includes a set of 3D coordinates for a plurality of body joints for each frame of the captured depth data. The electronic controller is also configured to detect movements of the first subject's body using the body motion data. The electronic controller is further configured to determine a set of attributes for the detected movements of the first subject's body using the body motion data. The electronic controller is also configured to extract facial motion data for a face of the first subject from the captured depth data. The facial motion data includes a set of 3D coordinates for a plurality of facial points for each frame of the captured depth data. The electronic controller is further configured to determine identification data for the first subject using the facial motion data. The electronic controller is further configured to create a session record for the first subject. The session record includes the body motion data, the detected movements of the first subject's body, the set of attributes, and the identification data for the first subject.

The disclosure further provides a method for markerless tracking of a subject performing a motor exercise. The method includes pre-storing a movement profile in a memory. The pre-stored movement profile includes a plurality of benchmarks. The method also includes capturing, with an active 3D infrared camera, depth data of a body of the subject during the motor exercise. The method further includes extracting, with an electronic processor, body motion data for the subject's body from the captured depth data. The body motion data includes a set of 3D coordinates for a plurality of body joints for each frame of the captured depth data. The method also includes detecting, with the electronic processor, movements of the subject's body using the body motion data. The method further includes determining, with the electronic processor, a set of attributes for the detected movements of the subject's body using the body motion data. The method also includes assigning, with the electronic processor, a rating for the motor exercise by comparing the set of attributes for the detected movements of the subject's body with the plurality of benchmarks included in the pre-stored movement profile. The method further includes creating, with the electronic processor, a session record for the subject. The session record includes the body motion data, the set of attributes for the detected movements of the subject's body, and the assigned rating.

Other aspects and embodiments will become apparent by consideration of the detailed description and accompanying drawings.

Figure 1:
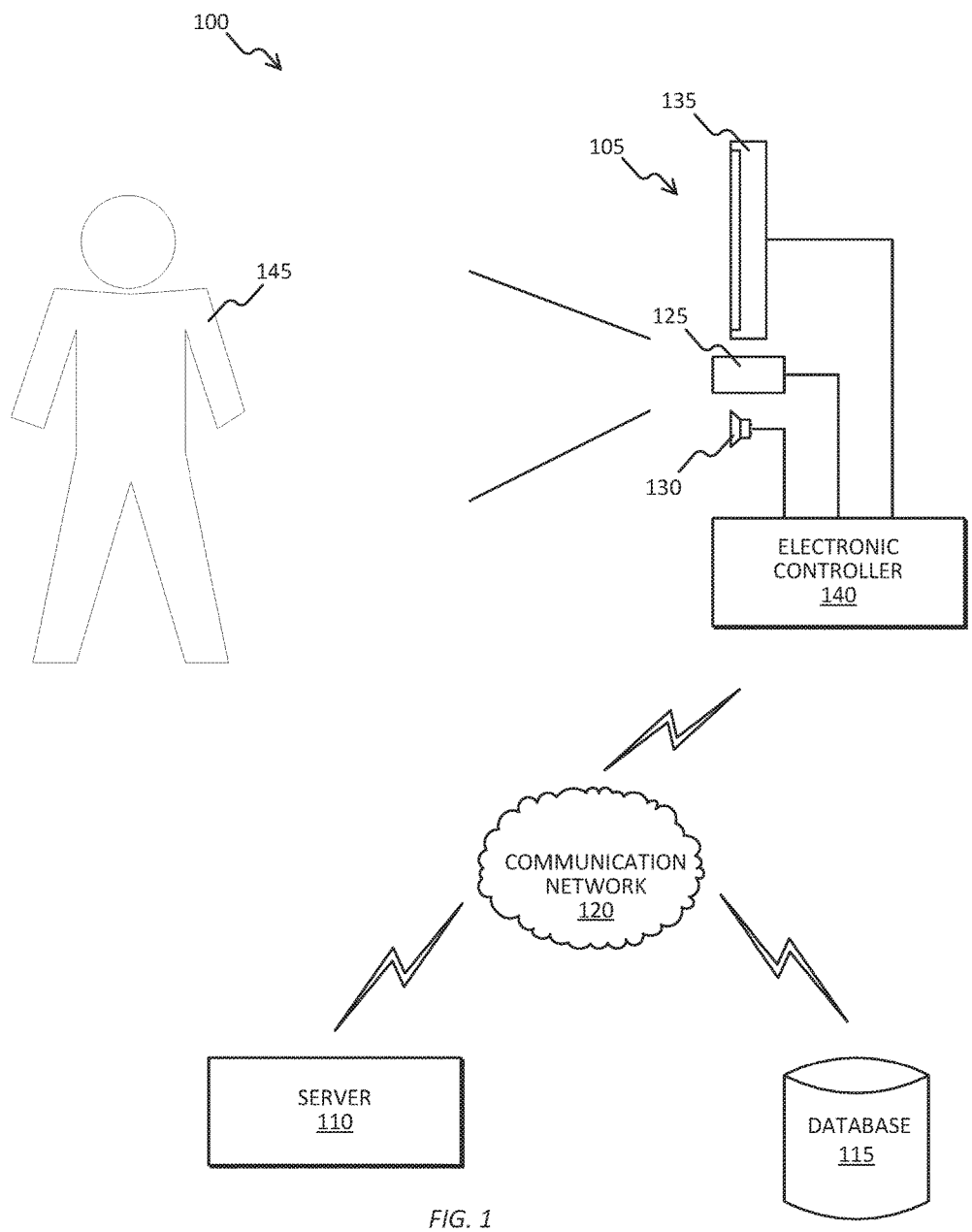
FIG. 1 is a diagram of a markerless tracking system, in accordance with some embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments illustrated.

The apparatus and method components have been represented where appropriate by conventional symbols in the drawings, showing only those specific details that are pertinent to understanding various embodiments so as not to obscure the disclosure with details that will be readily apparent to those of ordinary skill in the art having the benefit of the description herein.

DETAILED DESCRIPTION

Before any embodiments are explained in detail, it is to be understood that no embodiment is necessarily limited in its application to the details of construction and the arrangement of components set forth in the following description or illustrated in the following drawings. Other embodiments are possible and embodiments described are capable of being practiced or of being carried out in various ways.

It should also be noted that a plurality of different structural components may be utilized to implement the disclosure. Furthermore, and as described in subsequent paragraphs, the specific configurations illustrated in the drawings are intended to exemplify certain embodiments. Alternative configurations are possible.

For ease of description, the example systems presented herein may be illustrated with a single exemplar of each of their component parts. Some examples may not describe or illustrate all components of the systems. Other example embodiments may include more or fewer of each of the illustrated components, may combine some components, or may include additional or alternative components.

FIG. 1 is a diagram of one example embodiment of a markerless tracking system 100. In the embodiment illustrated in FIG. 1, the markerless tracking system 100 includes an electronic tracking device 105, a server 110, a database 115, and a communication network 120. The electronic tracking device 105 is illustrated in FIG. 1 as a combination of a sensor array 125, a speaker 130, a display screen 135, and an electronic controller 140. As described in more detail below, the electronic tracking device 105 records and evaluates, among other things, different types of motion data for a subject (for example, user 145 in FIG. 1).

The communication network 120 may be a wired network, a wireless network, or both. All or parts of the communication network 120 may be implemented using various networks, for example, a cellular network, the Internet, a Bluetooth™ network, a wireless local area network (for example, Wi-Fi), a wireless accessory Personal Area Networks (PAN), cable, an Ethernet network, satellite, a machine-to-machine (M2M) autonomous network, and a public switched telephone network. The electronic tracking device 105, the server 110, and the other various components of the markerless tracking system 100 communicate with each other over the communication network 120 using suitable wireless or wired communication protocols. In some embodiments, communications with other external devices (not shown) occur over the communication network 120.

The markerless tracking system 100 illustrated in FIG. 1 is provided as one example of such a system. The methods described herein may be used with tracking systems with fewer, additional, or different components in different configurations than the markerless tracking system 100 illustrated in FIG. 1. For example, in some embodiments, the markerless tracking system 100 includes fewer or additional electronic tracking devices, fewer or additional servers, and fewer or additional databases.

Figure 2:
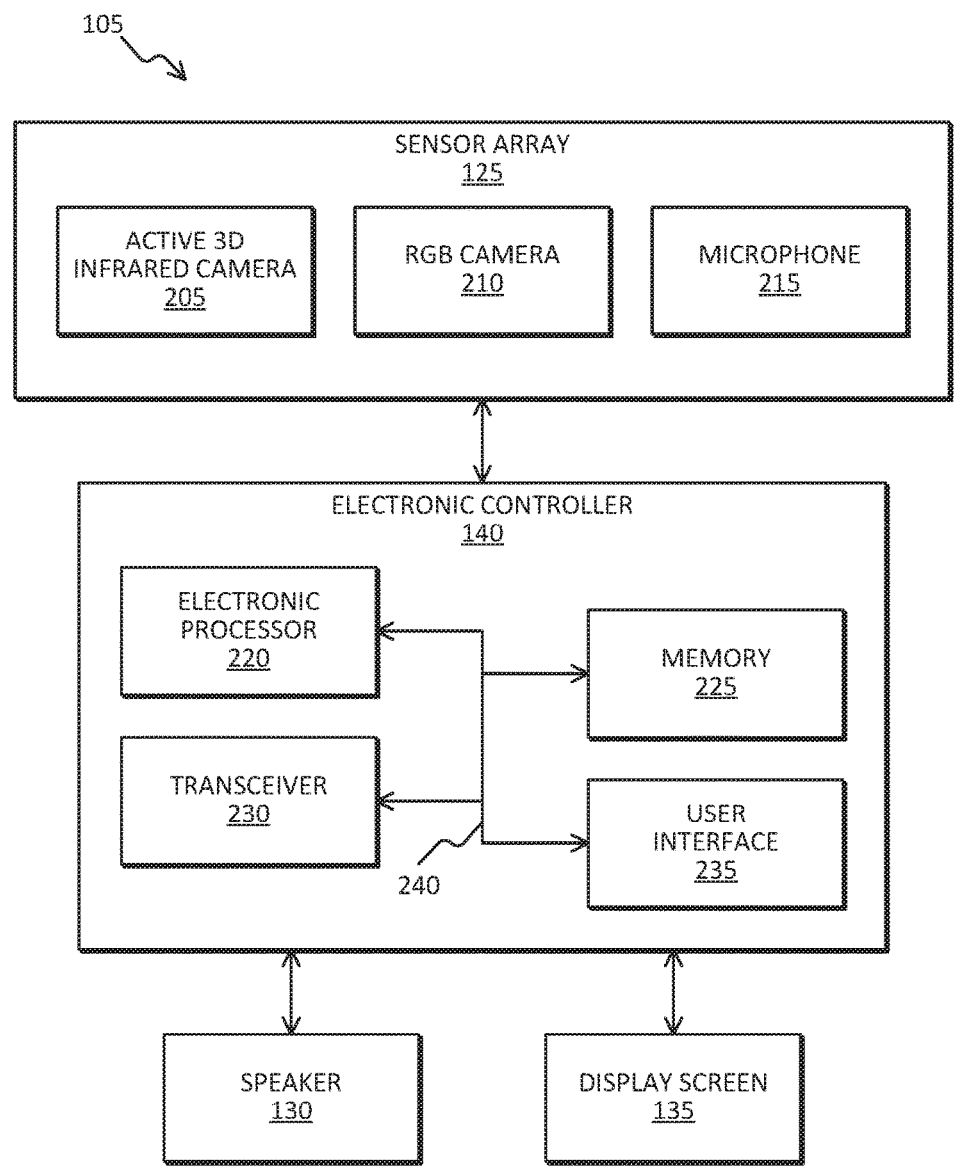
FIG. 2 is a diagram of an electronic tracking device included in the markerless tracking system of FIG. 1, in accordance with some embodiments.

FIG. 2 is a diagram of one example embodiment of the electronic tracking device 105 including the sensor array 125, the speaker 130, the display screen 135, and the electronic controller 140. In alternate embodiments, the electronic tracking device 105 may include fewer or additional components in configurations different from the configuration illustrated in FIG. 2.

The sensor array 125 illustrated in FIG. 2 includes an active 3D infrared camera 205, and a red-green-blue (RGB) camera 210, and a microphone 215. In some embodiments, the active 3D infrared camera 205, the RGB camera 210, and the microphone 215 are commonly located in the same sensory array housing, as illustrated in FIGS. 1 and 2. Alternatively, active 3D infrared camera 205, the RGB camera 210, and the microphone 215 may be located in separate housings.

The active 3D infrared camera 205 captures depth data of a subject's body (for example, while the subject is performing a motor exercise). The captured depth data includes a stream of depth image frames. Each pixel in each frame of the captured depth data indicates the distance between an object and a specific pixel point of the active 3D infrared camera 205 at a specific time. The active 3D infrared camera 205 outputs the captured depth data to the electronic controller 140.

The active 3D infrared camera 205 (for example, a 3D time-of-flight camera) includes at least one infrared light emitter that emits infrared light and at least one infrared light detector that detects the infrared light's reflection off of objects located in front of the active 3D infrared camera 205. In some embodiments, the active 3D infrared camera 205 includes a 3D time-of-flight camera that determines the depth data by measuring the time-of-flight of the infrared light between the camera and an object. Example active 3D infrared cameras for use in the markerless tracking system 100 disclosed herein include Kinect™ (v2) by Microsoft™, the RealSense™ 3 D camera by Intel™, the structure sensor by Occipital, and the Lumix 3D camera by Panasonic™.

The active 3D infrared camera 205 enables non-obtrusive body motion tracking of a subject without markers. Some other body tracking systems require placing a plurality of markers on a subject's body. However, marker-based body tracking systems have several drawbacks. Placing the markers on the subject's body is time-consuming. In addition, subjects with neurological diseases typically suffer from motor impairments which make it difficult for them to attach markers to their bodies without assistance. Further, the presence of markers on the subject's body while the subject is performing motor exercises can alter the subject's movements.

The RGB camera 210 includes one or more optical sensors that capture and convert incident light within the human visible spectrum into electrical signals. For example, the RGB camera 210 includes charged-coupled devices (CCDs) or complementary metal-oxide-semiconductor (CMOS) devices that capture a color image, a sequence of color images, video, and the like. In some embodiments, the RGB camera 210 captures a sequence of color images of the subject's body (for example, while the subject is performing the motor exercise). The microphone 215 detects sound and outputs analogous electric signals representing the sound to the electronic controller 140. The speaker 130 receives electric signals from the electronic controller 140 and outputs sound. The display screen 135 displays visual output generated by software applications executed by the electronic controller 140. Visual output includes, for example, graphical indicators, lights, colors, text, images, internet webpages, graphical user interfaces (GUIs), combinations of the foregoing, and the like. The display screen 135 includes a suitable display mechanism for displaying the visual output (for example, a light-emitting diode (LED) screen, a liquid crystal display (LCD) screen, an organic LED (OLED) screen, and the like).

The electronic controller 140 illustrated in FIG. 2 includes an electronic processor 220 (for example, a microprocessor), a memory 225, a transceiver 230, and a user interface 235. The electronic processor 220, the memory 225, as well as the other various modules are coupled by a bus 240, or are coupled directly, by one or more additional control or data buses, or a combination thereof. The memory 225 may include read only memory (ROM), random access memory (RAM), other non-transitory computer-readable media, or a combination thereof. The electronic processor 220 is configured to retrieve program instructions and data from the memory 225 and execute, among other things, instructions to perform the methods described herein.

The transceiver 230 transmits signals to the communication network 120 and receives signals from the communication network 120. Signals may include, for example, information, data, serial data, data packets, analog signals, or a combination thereof. The transceiver 230 can be coupled to one or more separate transceivers via wires, fiber, wirelessly, or a combination thereof. In some embodiments, the transceiver 230 includes separate transmitters and receivers.

The user interface 235 is included to control the electronic tracking device 105 or the operation of the markerless tracking system 100 as a whole. The user interface 235 can include any combination of digital and analog input devices required to achieve a desired level of control for the system.

In some embodiments, the user interface 235 includes a touch sensitive interface. For example, in some embodiments, the display screen 135 is a touch-screen display that receives user input using detected physical contact (for example, detected capacitance or resistance). Based on the user input, the display screen 135 outputs signals to the electronic processor 220 which indicate positions on the display screen 135 currently being selected by physical contact. Alternatively or in addition, the user interface 235 receives user input from a plurality of input devices such as a keyboard, a mouse, a trackpad, the microphone 215, and the like. In some constructions, the user interface 235 is separated from the electronic controller 140.

Figure 3:
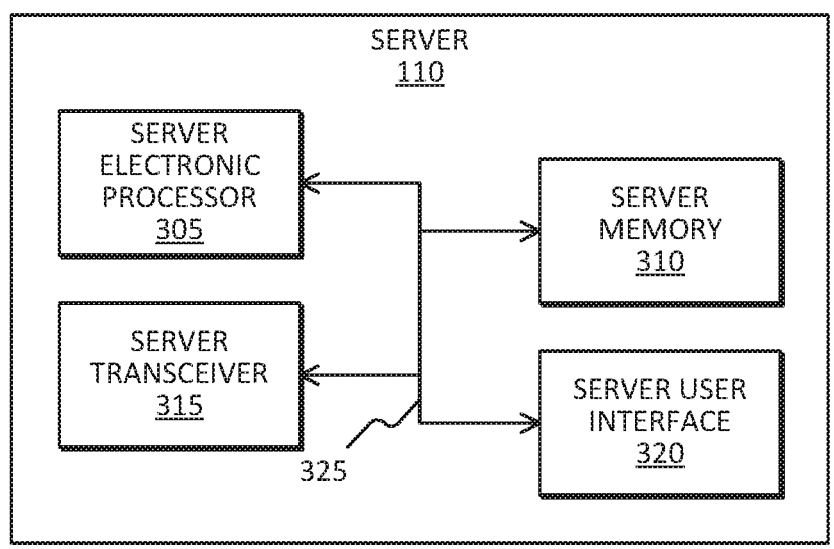
FIG. 3 is a diagram of a server included in the markerless tracking system of FIG. 1, in accordance with some embodiments.

FIG. 3 is a diagram of one example embodiment of the server 110. In the example illustrated, the server 110 includes a server electronic processor 305, server memory 310, a server transceiver 315, and a server user interface 320. The server electronic processor 305, the server memory 310, as well as the other various modules are coupled by a bus 325, or are coupled directly, by one or more additional control or data buses, or a combination thereof. In other embodiments, the server 110 may include fewer or additional components in configurations different from that illustrated in FIG. 3.

The server memory 310 stores program instructions and data. The server memory 310 may include combinations of different types of memory, including the various types of memory described above with respect to the memory 225 included in the electronic tracking device 105. The server electronic processor 305 retrieves program instructions from the server memory 310 and executes the instructions to perform a set of functions including all or part of the methods described herein. The server transceiver 315 transmits signals to and receives signals from the electronic tracking device 105 and the other components included in the markerless tracking system 100, such as through the communication network 120 or directly. The server user interface 320 includes any combination of digital and analog input devices required to achieve a desired level of control for the server 110. For example, the server user interface 320 can include a computer having a display and input devices, a display, a keyboard, a mouse, speakers, and the like.

In some embodiments, the database 115 may include components or combinations of different components, including all or some of the various components described above with respect to the server 110.

As discussed above, established rating scales for subjects with Parkinson's disease (or other neurological diseases) typically include a series of motor exercises. Currently, a doctor watches a subject performing each of the motor exercises and then determines a rating for the subject's movement based on a series of prescribed guidelines. However, there is a need for a reliable system of capturing and objectively evaluating a subject's performance of motor exercises without requiring a doctor to be present. As described below in more detail, the markerless tracking system 100 records and automatically evaluates a subject's performance of a motor exercise.

Figure 4:
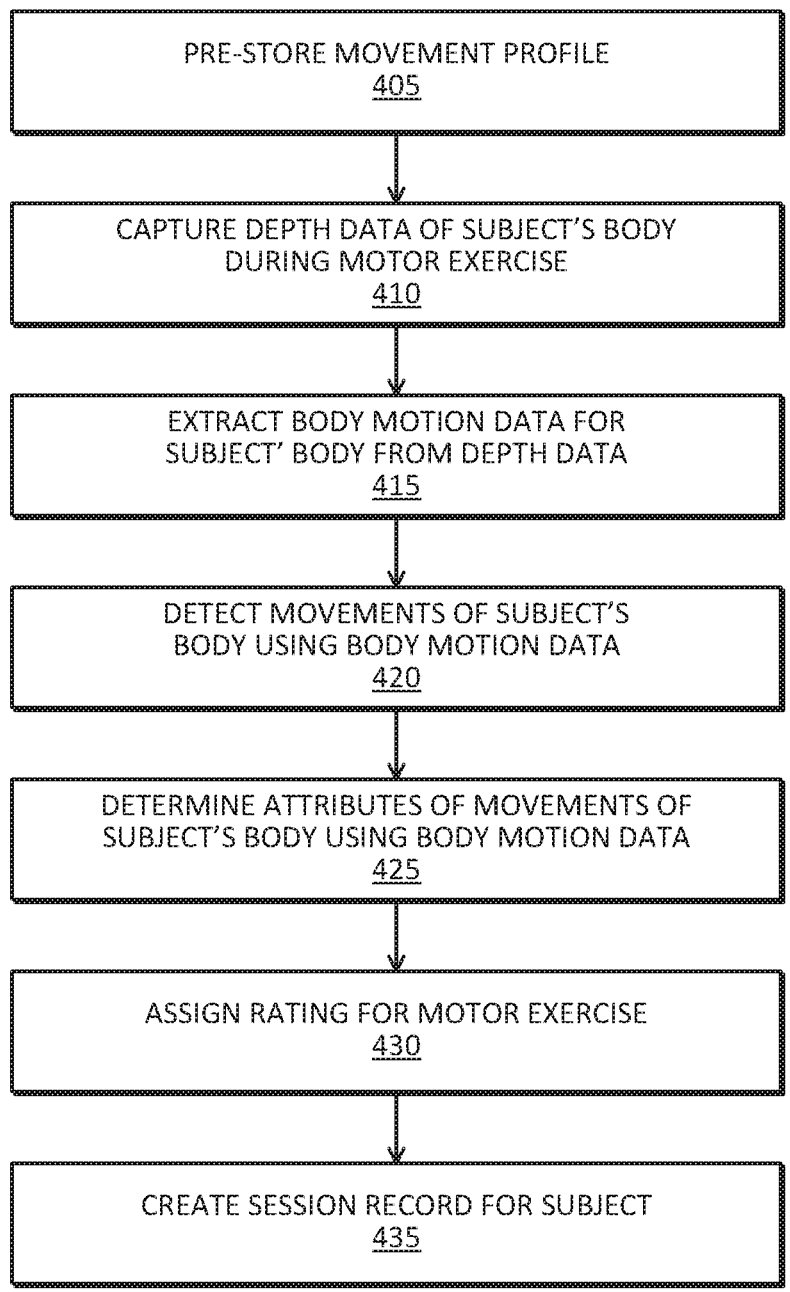
FIG. 4 is a flowchart of a method for markerless tracking of a subject performing a motor exercise with the electronic tracking device of FIG. 2, in accordance with some embodiments.

FIG. 4 is an example embodiment of a method 400 for markerless tracking of a subject performing a motor exercise. At block 405, a movement profile is pre-stored, for example, in the memory 225 of the electronic controller 140. The movement profile includes a plurality of benchmarks for at least one motor exercise. Each benchmark defines a set of conditions and a rating for a motor exercise that are associated with a specific mobility level. Table #1 illustrates an example of benchmarks for a toe tapping motor exercise in which the subject taps their toe 10 times as fast as possible. The example benchmarks illustrated in Table #1 include scales for rating the motor exercise based on the number of interruptions (for example, halts and hesitations), reductions in speeds, and reductions in amplitude. For example, 3 to 5 interruptions in the tapping movements indicate a rating of 2.

TABLE #1

Example Benchmark for a Toe Tapping Motor Exercise

| Interruptions | Speed Reduction (kilometers per hour) | Amplitude Reduction (centimeters) | Rating |
|---|---|---|---|
| 0 | 0.0-0.1 | 0-2 | 0 |
| 1-2 | 0.1-0.3 | 3-5 | 1 |
| 3-5 | 0.4-0.6 | 6-8 | 2 |
| 5-7 | 0.7-0.9 | 9-11 | 3 |
| 8+ | 1.0+ | 12+ | 4 |

The movement profile may be generated based on established rating scales. In some embodiments, the plurality of benchmarks included in the movement profile are standard benchmarks that apply to all subjects with a specific neurological disease. Alternatively or in addition, the plurality of benchmarks included in the movement profile are specifically tailored to the subject. In some embodiments, the movement profile includes benchmarks for a plurality of motor exercises. In some embodiments, the electronic controller 140 obtains the movement profile (or a portion thereof) from the server 110, the database 115, or both.

At block 410, the active 3D infrared camera 205 captures depth data of a subject's body while the subject is performing the motor exercise. As described above, the depth data includes a stream of depth image frames. Each depth image frame indicates the positions of the subject's body at a specific time. The frame rate of the depth data is at least 30 frames per second. In some embodiments, the frame rate of the depth data is approximately 60 frames per second.

Figure 5:
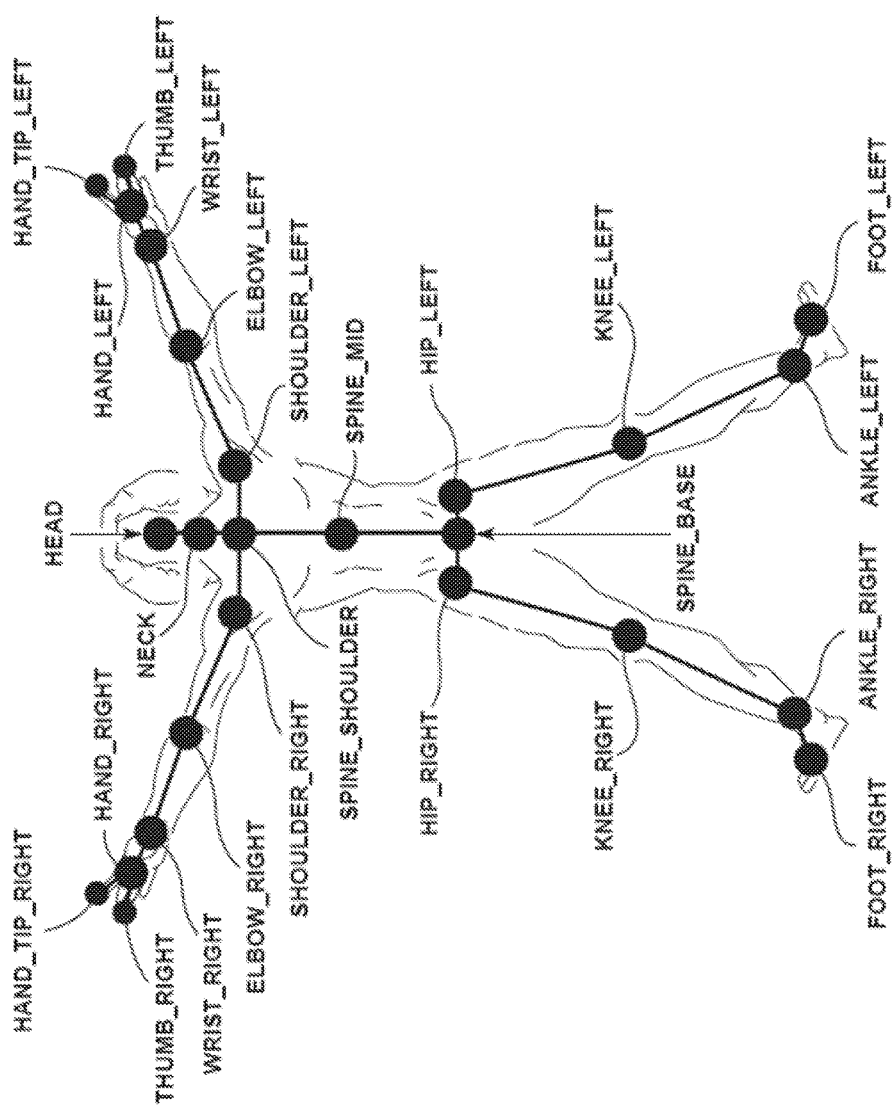
FIG. 5 is a diagram of a plurality of body joints on a subject's body, in accordance with some embodiments.

At block 415, the electronic processor 220 extracts body motion data for the subject's body using the depth data. The body motion data includes a set of 3D coordinates (for example, X, Y, and Z) for a plurality of body joints on the subject's body for each frame of the depth data. FIG. 5 illustrates an example plurality of body joints. Each of the 3D coordinates indicates the three-dimensional position of a body joint at a specific time.

Body joint tracking is most accurate when the active 3D infrared camera 205 has a direct line of sight to every tracked body joint. In practice, the position of the subject's body may prevent the active 3D infrared camera 205 from having a direct line of sight with every tracked body joint. For example, the subject's body may be positioned such that subject's torso is blocking the active 3D infrared camera's 205 view of the subject's left hand. In some embodiments, the body motion data includes a tracking state for each of the 3D coordinates. The tracking state can indicate whether the associated body joint is tracked, inferred, or not tracked. The "tracked" tracking state can indicate that the active 3D infrared camera 205 has a direct view of a body joint. The "inferred" tracking state can indicate that the active 3D infrared camera 205 has a partial view of a body joint. The "not tracked" tracking state can indicate that the active 3D infrared camera 205 does not have a view of a body joint.

Returning to FIG. 4, at block 420, the electronic processor 220 detects movements of the subject's body using the body motion data. Movements of the subject's body include, among other things, movements of a specific portion of the subject's body (for example, tapping a finger, tapping a foot, or making a fist), combined movements of multiple parts of the subject's body (for example, extending an arm out or raising a leg off the ground), and movements of the subject's entire body (for example, walking with arm swing or arising from a chair). In some embodiments, the electronic processor 220 detects movement of the subject's body by comparing the body motion data to predetermined movement models stored in the memory 225.

At block 425, the electronic processor 220 determines attributes for the detected movements of the subject's body using the body motion data. Attributes include, for example, speed, acceleration, amplitude, number of iterations, max height, number of hesitations, number of halts, rhythm, duration, and stride length. In some embodiments, the electronic processor 220 selects the attributes to determine based on the motor exercise. For example, with the toe tapping motor exercise described above, the electronic processor 220 may select to determine the number of iterations, the speed, the amplitude, the number of hesitations, and the number of halts.

In some embodiments, the electronic processor 220 using a centroid-based approach to determine the set of attributes for the detected movements of the subject's body. As a first example, the electronic processor 220 determines a speed attribute for a foot stomping motor exercise in which the subject raises and stomps their left foot on the ground 10 times as high and as fast as possible. The electronic processor 220 selects a subset of the plurality of body joints including the subject's left knee, left ankle, and left foot. The electronic processor 220 determines a centroid position for each frame of the depth data using the 3D coordinates of the subject's left knee, left ankle, and left foot extracted from the depth data. The electronic processor 220 then determines the speed of the subject's movements based on the changes in the determined centroid positions over time.

As a second example, for determining an amplitude attribute for the foot stomping motor exercise, the electronic processor 220 selects a subset of the plurality of body joints including subject's left ankle and left foot. The electronic processor 220 determines a centroid position for each frame of the depth data using the 3D coordinates of the subject's left ankle and left foot extracted from the depth data. The electronic processor 220 then determines the amplitude of each leg raising movement based on the highest calculated position of the centroid.

Returning to FIG. 4, at block 430, the electronic processor 220 assigns a rating to the motor exercise by comparing the set of attributes for the movements of the subject's body to the plurality of benchmarks included in the pre-stored movement profile. As described above, each benchmark defines a set of conditions and a rating for a motor exercise that are associated with a specific mobility level. In some embodiments, the electronic processor 220 compares the set of attributes to the set of conditions and determines the lowest mobility rating with at least one condition met by the set of attributes. For example, with respect to Table #1, when the set of attributes includes 4 interruptions, a speed decrease of 0.2 kilometers per hour, and an amplitude decrease of 3 centimeters for a motor exercise, the electronic processor 220 assigns a rating of 2 for the motor exercise.

In some embodiments, the electronic processor 220 determines a rating for each attribute of the movements of the subject's body and averages the determined ratings to determine an overall rating for the motor exercise. For example, with respect to Table #1, when the electronic processor 220 determines 4 interruptions, a speed decrease of 0.2 kilometers per hour, and an amplitude decrease of 3 centimeters for a motor exercise, the electronic processor 220 assigns a rating of 1 for the motor exercise.

At block 435, the electronic processor 220 creates a session record for the subject. The session record is a collection of data which provides various information about a subject's performance of a motor exercise. The session record is stored (for example, in the memory 225, in the server memory 310, or in the database 115) such that it can be later accessed for review, analysis, or comparison to other session records. In some embodiments, the session record may be combined with other information of the subject that is included in an electronic health record (EHR).

Figure 6:
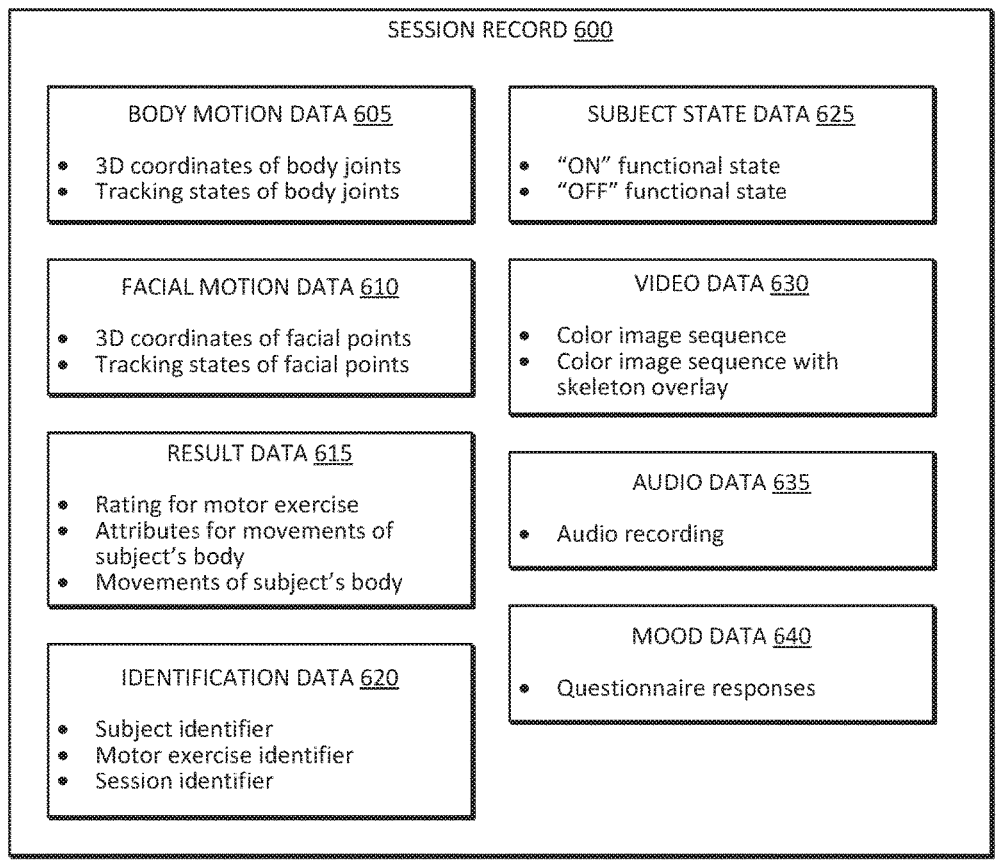
FIG. 6 is a diagram of session record created by the electronic tracking device of FIG. 2, in accordance with some embodiments.

FIG. 6 is a diagram of one example embodiment of a session record 600 for a subject. In the example illustrated in FIG. 6, the session record 600 includes body motion data 605, facial motion data 610, result data 615, identification data 620, subject state data 625, video data 630, audio data 635, and mood data 640. In other embodiments, a session record may include fewer or additional components in configurations different from that illustrated in FIG. 6.

The body motion data 605 includes all (or any portion) of the sets of 3D coordinates for the plurality of body joints that the electronic processor 220 extracts from each frame of the depth data captured by the active 3D infrared camera 205. As described above, each of the 3D coordinates indicate the three-dimensional position of a body joint at a specific time. In some embodiments, the body motion data 605 also includes the tracking states for all (or any portion) of the 3D coordinates for the plurality of body joints.

Figure 7:
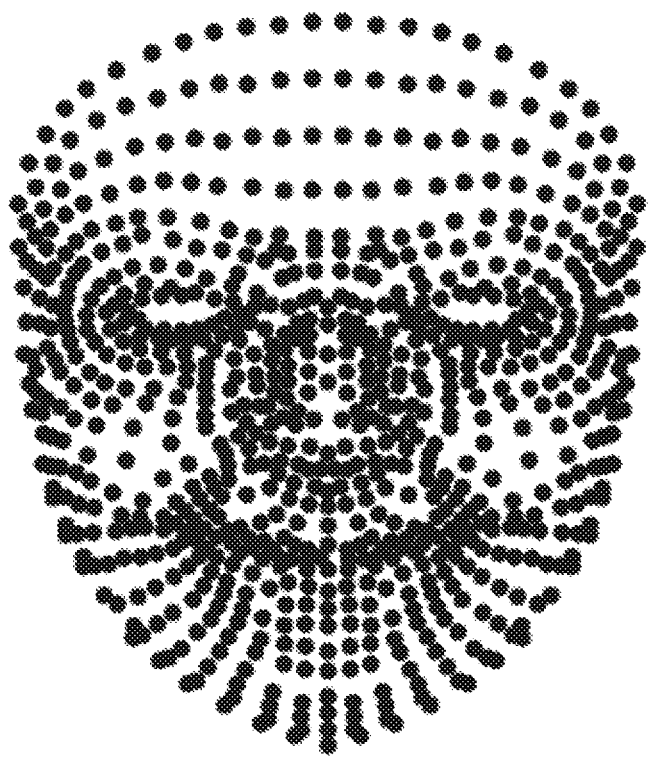
FIG. 7 is a diagram of a plurality of facial points on a subject's body, in accordance with some embodiments.

In some embodiments, in addition to the body motion data 605, the electronic processor 220 also extracts facial motion data 610 for the subject's face from the depth data captured by the active 3D infrared camera 205. The facial motion data 610 includes a set of 3D coordinates (for example, X, Y, and Z) for a plurality of facial points on the subject's face for each frame of the depth data. FIG. 7 illustrates an example plurality of facial points. In some embodiments, the facial motion data 610 also includes tracking states for all (or any portion) of the 3D coordinates for the plurality of facial points.

The result data 615 includes, among other things, the rating for the motor exercise assigned by the electronic processor 220, the set of attributes for movements of the subject's body determined by the electronic processor 220, the movements of the subject's body detected by the electronic processor 220, or a combination thereof.

The identification data 620 includes, among other things, a subject identifier, a motor exercise identifier, a session identifier, or a combination thereof. The subject identifier identifies the subject performing the motor exercise. The subject identifier may include, for example, a unique identification number assigned to the subject, the subject's name, the subject's date of birth, the subject's gender, the subject's telephone number, the subject's e-mail address, or a combination thereof. The motor exercise identifier indicates the specific motor exercise performed by the subject. For example, one motor exercise identifier can indicate that the subject is performing a finger tapping motor exercise and another motor exercise identifier can indicate that the subject is performing an arising from chair motor exercise. In some embodiments, one session record can include data for multiple motor exercises performed by the subject in a single session. For example, the subject may sequentially perform several motor exercises in a single session. In such embodiments, the identification data 620 may include separate motor exercise identifier for each motor exercise performed by the subject. The session identifier differentiates one session record from another. The session identifier may include, for example, a unique identification number for the session, a time stamp, or both.

Subjects with neurological diseases, such as Parkinson's disease, often experience decreased motor functionality over time. The decreased motor functionality can be tracked by comparing measured attributes of motor exercises from different session records. In addition, subjects with neurological diseases typically take medication to limit mobility symptoms. The session records may also be used to determine the effect of different medications on the mobility of a patient.

Subjects with neurological diseases often have periods of time in which their mobility is impaired in spite of taking medication. A subject is considered to be in an ON functional state when they are taking medication and having a good response. A subject is considered to be in an OFF functional state when they are having a poor response in spite of taking medication. The subject state data 625 indicates whether the subject is in the ON functional state or in the OFF functional state while performing the motor exercise. In some embodiments, the electronic processor 220 determines the subject's functional state by comparing the set of attributes determined for the subject's current performance of the motor exercise with a set of attributes determined for a prior performance of the motor exercise by the subject. In some embodiments, the electronic processor 220 may retrieve the set of attributes determined for the subject's prior performance of the motor exercise (for example, a second set of attributes) from the memory 225. The electronic processor 220 determines whether the subject is in the ON functional state or in the OFF functional state based on a difference between the set of attributes determined for the subject's current performance of the motor exercise and the second set of attributes. For example, a large deviation between the amplitude of movements for the current performance of the motor exercise and the amplitude of movements for a prior performance of the motor exercise may indicate that the subject is in the OFF functional state.

Many neurological diseases are individual to each subject. Each subject with the same neurological disease can experience a unique progression of mobility impairment. Thus, a movement profile that includes standard benchmarks for all subjects with same neurological disease may not provide the best rating scale for identifying a subject's unique progression of mobility impairment. In some embodiments, the markerless tracking system 100 adjusts one or more of the standard benchmarks included in the movement profile based on user input. User input may include, for example, a second rating for a motor exercise provided by a doctor via the user interface 235. The electronic processor 220 may compare the second rating for the motor exercise with the rating for the motor exercise assigned by the electronic processor 220 to identify any differences. In some embodiments, the electronic processor 220 adjusts at least one of the plurality of benchmarks included in the movement profile based on the determined difference between the two ratings for the motor exercise.

The second rating for the motor exercise may be received via the user interface 235 while the subject is performing the motor exercise or immediately after. However, in order to remove the requirement for a doctor to be physically present while the subject is performing the motor exercise, in some embodiments, all (or a portion) of the sequence of color images captured by the RGB camera 210 of the subject performing the motor exercise is included in the session record 600 as video data 630. Adding the sequence of color images to the session record 600 enables a doctor to view subject's performance of the motor exercise and provide their own rating at a later time and at a different location.

Figure 8:
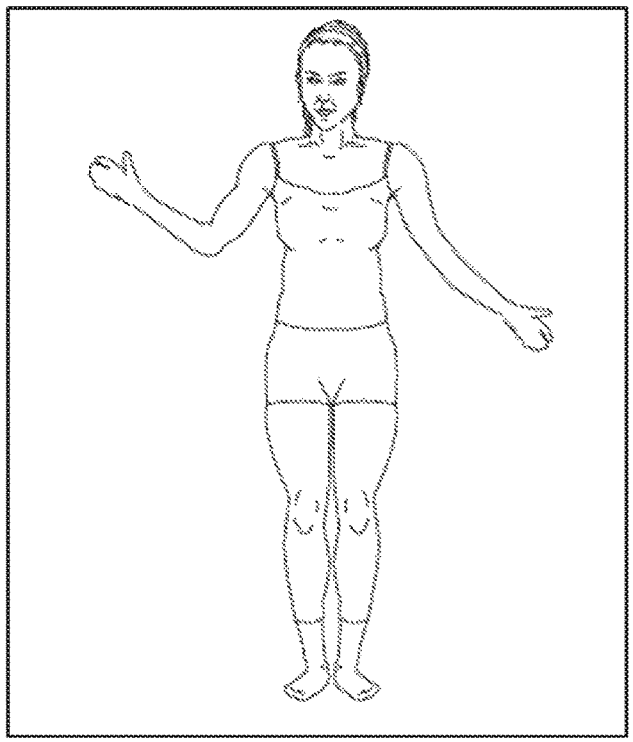
FIG. 8 is an example of a color image of a subject's body captured by the electronic tracking device of FIG. 2, in accordance with some embodiments.
Figure 9:
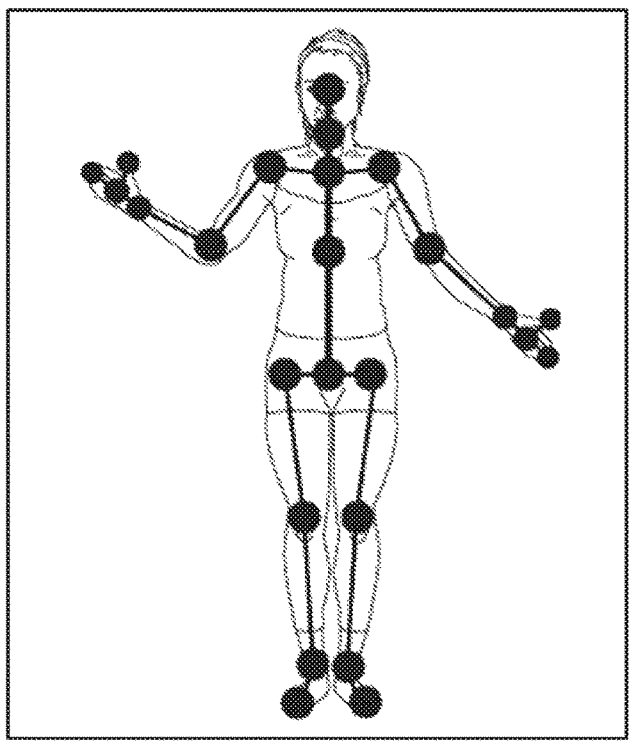
FIG. 9 is the color image of FIG. 8 with a skeleton overlay, in accordance with some embodiments.

Alternatively, or in addition, the electronic processor 220 alters the sequence of color images by superimposing a skeleton over the subject's body indicating the current positions of the plurality of body joints. For example, FIG. 8 is an example color image of a subject's body captured by the RGB camera 210. In FIG. 9, a skeleton depicting the body motion data 605 is superimposed on the color image. Altering the sequence of color images to include skeleton overlays as described above enables future validation and additional analysis of the patient's performance of the motor exercise. For example, a doctor or medical technician may view the sequence of altered color images and use the skeleton overlay to confirm that the body motion data 605 accurately reflects the movements of the subject's body while the subject is performing the motor exercise. In addition, the skeleton overlay can assist a doctor in determining their own rating for the motor exercise by providing a video with clearer indications of the subject's movements during the motor exercise.

While the active 3D infrared camera 205 and the RGB camera 210 have overlapping fields of view of the subject's body, they are positioned apart from each other and their spatial references to features of the subject's body are not the same. For example, the coordinates of a body joint in a depth image frame from the active 3D infrared camera 205 will be offset from the coordinates of the same body joint in a corresponding color image from the RGB camera 210. The position of the RGB camera 210 relative to the position of the active 3D infrared camera 205 is known and fixed. Thus, in some embodiments, for each color image, the electronic processor 220 calculates corresponding 2D coordinates in the color image for each of the plurality of body joints using the body motion data 605 and prior knowledge of the locations and the fields of view of the cameras. The electronic processor 220 then alters the color image by superimposing a skeleton on the color image. The skeleton includes, among other things, visual indicators at the calculated 2D coordinates for each of the plurality of body joints of the subject's body, as illustrated in FIG. 9.

Returning to FIG. 6, the audio data 635 includes, among other things, all (or any portion) of the sound recorded by the microphone 215 while the subject is performing the motor exercise. Subjects with Parkinson's diseases (or other neurological diseases) can suffer from impaired speech. In some embodiment, the electronic processor 220 (or the server 110) analyzes the audio data 635 to identify any speech problems. For example, the electronic processor 220 may analyze the audio data 635 to identify any loss of modulation, diction, or volume.

The mood data 640 includes data indicating non-movement symptoms of the subject. As described above, some established rating scales for subjects with neurological diseases include questionnaires. For example, questionnaires such as the PD NMS questionnaire, the PDQ-39, and the PDQ-8 are utilized for subjects with Parkinson's disease. The PD NMS questionnaire is used to detect non-motor symptoms. The PDQ-39 and PDQ-8 are each a set of questions that are used to capture feedback from a subject regarding the subject's quality of life. In some embodiments, the electronic processor 220 administers a questionnaire to the subject by displaying questions on the display screen 135 and receiving the subject's responses via the user interface 235. The mood data 640 includes the subject's responses to a questionnaire.

In some embodiments, the electronic processor 220 is cognizant of the current motor exercise being performed by the subject prior to the subject performing it. For example, the electronic processor 220 may determine the current motor exercise based on user input received via the user interface 235 or the transceiver 230. Alternatively or in addition, the electronic processor 220 identifies the current motor exercise based on the movements of the subject's body detected using the body motion data 605. For example, by comparing the detected movements of the subject's body to a set of predetermined reference movements included in some embodiments of the movement profile, the electronic processor 220 may determine that the subject is performing a toe tapping motor exercise.

As described above, current evaluation methods for subjects with Parkinson's disease require a doctor to be present to administer the evaluation. Thus, subjects with Parkinson's disease are typically evaluated only once or twice a year when during visits to their doctor. This frequency of evaluation does not provide doctors with enough information to make informed decisions about the efficacy of treatments being provided to subjects. By recording and automatically evaluating subjects' performances of motor exercises, the markerless tracking system 100 can be used to evaluate subjects with Parkinson's disease using established rating scales without requiring a doctor to be present. Not needed a doctor to be present enables evaluations to be conducted more often because a subject can perform the evaluations in their own home. More frequent evaluations enable better tracking of the progression of neurological diseases. More frequent evaluations also give doctors more information about the efficacy of different treatments and medications.

In addition, the markerless tracking system 100 can be used to provide objectivity in evaluating subjects with Parkinson's disease. As described above, current evaluation methods utilize a doctor's eyeball judgements of a subject's performances of motor exercises. On the other hand, the markerless tracking system 100 rates a subject's performance of a motor exercise by calculating attributes that cannot be accurately determined by eyeball judgement, such as speed and distance. Thus, the markerless tracking system 100 brings objectivity to subjectivity in evaluating subjects with Parkinson's disease.

Further, the markerless tracking system 100 can be used for early detection of neurological diseases. For Parkinson's disease, a subject's body typically has already lost about 50 to 70 percent of its dopamine by the time a clinic diagnosis is made. The markerless tracking system 100 can be used to identify decreases in a subject's motor functions, which can be an early indicator of Parkinson's disease.

In some embodiments, the server 110 (or the electronic controller 140) includes (or implements) a machine learning engine that can assign a disease (or physical) state to a subject by evaluating a plurality of session records of the subject. The machine learning engine evaluates feedback from medical professionals (for example, a second rating for a motor exercise provided by a doctor, annotated clinician report, etc.) to train a classifier of the machine learning engine. For example, in reference to Parkinson's disease, the machine learning engine matches the second rating for a motor exercise provided by a doctor with the captured body motion data 605 to train the classifier. The machine learning engine identifies and extracts raw motor features associated with each motor exercise. The machine learning engine models these raw motor features collected from various subjects (including subjects in various disease states, control subjects who are healthy, or both) in order to differentiate between different ratings for motor exercises, and to generate and adjust the plurality of benchmarks in the movement profile. The markerless tracking system 100 can use the machine learning engine to predict the neurological disease state (or present physical abnormality) of a subject in substantially real time using data captured by the markerless tracking system 100 including, among other things, body motion data 605, facial motion data 610, result data 615, subject state data 625, mood data 640, or a combination thereof.

Figure 10:
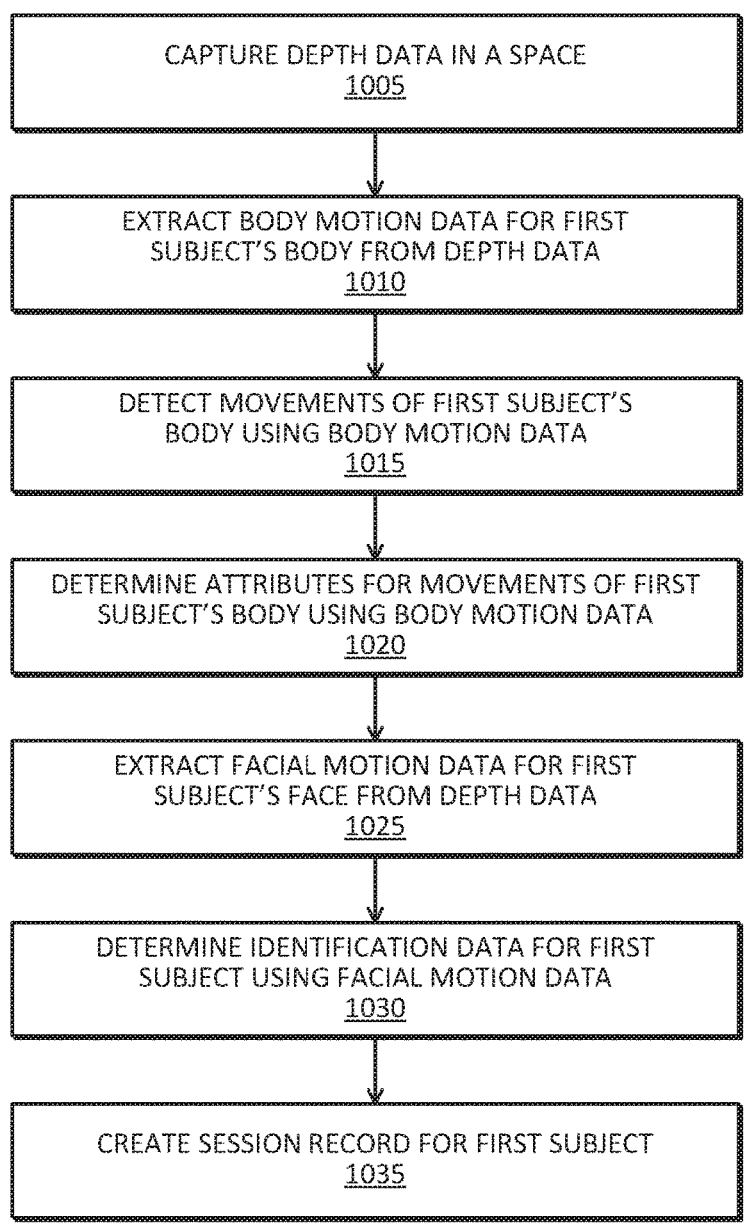
FIG. 10 is a flowchart of a method for markerless tracking in a space with the electronic tracking device of FIG. 2, in accordance with some embodiments.

In addition to tracking motor exercises performed by subjects, the markerless tracking system 100 described herein can also be used for tracking of passive motion of subjects located in a space (for example, in a room). FIG. 10 is one example embodiment of a method 1000 for markerless tracking of subjects located in a space. At block 1005, the active 3D infrared camera 205 captures depth data in the space. As described above, the depth data includes a stream of depth image frames.

At block 1010, the electronic processor 220 extracts body motion data for a body of a first subject located in the space using the depth data. The body motion data includes a set of 3D coordinates (for example, X, Y, and Z) for a plurality of body joints on the subject's body for each frame of the depth data.

At block 1015, the electronic processor 220 detects movements of the first subject's body using the body motion data. Detected movements of the first subject's body include, among other things, movements such as those described above in relation to block 420 in FIG. 4. In some embodiments, the electronic processor 220 detects movement of the first subject's body by comparing the body motion data to predetermined movement models stored in the memory 225.

At block 1020, the electronic processor 220 determines attributes for the movements of the first patient's body using the body motion data. Attributes include, for example, speed, acceleration, amplitude, number of iterations, max height, number of hesitations, number of halts, rhythm, duration, and stride length. In some embodiments, the electronic processor 220 selects the attributes to determine based on the detected movements of the first subject's body. For example, the electronic processor 220 may select to determine speed and stride length when the electronic processor 220 detects that the first subject is walking.

At block 1025, the electronic processor 220 extracts facial motion data for a face of the first subject using the depth data. The facial motion data includes a set of 3D coordinates (for example, X, Y, and Z) for a plurality of facial points on the first subject's face for each frame of the depth data.

At block 1030, the electronic processor 220 determines identification data for first the subject using the facial motion data. In some embodiments, the identification data includes one or more identifiers for the first subject which the electronic processor 220 determines using the facial motion data. For example, the electronic processor 220 may determine characteristics of the first subject's face such as the distance between the eyes, the width of the nose, the depth of the eye sockets, the shape of the cheekbones, and the length of the jaw line. The electronic processor 220 then compares the determined characteristics of the first subject's face to facial records of multiple subjects stored, for example, in the memory 225. After identifying a matching facial record to the determined characteristics of the first subject's face, the electronic processor 220 accesses one or more identifiers for the first subject included in the facial record. Identifiers for a subject include, for example, a unique identification number assigned to the subject, the subject's name, the subject's identification number, the subject's date of birth, the subject's phone number, and the subject's e-mail address. Alternatively or in addition, the identification data may include the characteristics of the first subject's face, which the electronic processor 220 determines using the facial motion data. By including the determined characteristics of the first subject's face in the identification data, the identity of the first subject can be later determined, for example, by the server 110.

Gait characteristics can also be used to identify the first subject. Gait is the manner in which a subject walks (for example, arm swing, pace, and stride length). In general, the gait of every person is different. In some embodiments, gait characteristics are used to identify the first subject. For example, the electronic processor 220 may determine gait characteristics of the first subject using the body motion data, the facial motion data, or both. The electronic processor 220 then compares the determined gait characteristics of the first subject gait records of multiple subjects stored, for example, in the memory 225. After identifying a matching gait record to the determined gait characteristics of the first subject, the electronic processor 220 accesses one or more identifiers for the first subject included in the gait record.

Returning to FIG. 10, at block 1035, the electronic processor 220 creates a session record for the first subject. The session record includes, for example, the body motion data, the detected movements of the first subject's body, the determined set of attributes for the detected movements of the first subject's body, the identification data for the first subject, video data (similar to the video data 630 described above in relation to FIG. 6), audio data (similar to the audio data 635 described above in relation to FIG. 6), or a combination thereof. In some embodiments, the electronic processor 220 stores the session record for the first subject in the memory 225. Alternatively or in addition, the electronic processor 220 sends the session record for the first subject to the server 110, the database 115, or both.

By determining identification data for a subject using facial motion data and included the determined identification data in the session record, as described above in relation to method 1000, the markerless tracking system 100 described herein can also be used for tracking of passive motion of multiple subjects located in a space. For example, the electronic processor 220 can perform steps similar to those described above in method 1000 to create a separate session record for a second subject located in the space. The unique identification data included in each session record can be used to later identify the subject to which a specific session record applies.

With the methods for tracking of passive motion of subjects as described above, the markerless tracking system 100 can be used in sports and physical rehabilitation applications. For example, the markerless tracking system 100 can be used to capture motion data and video of athletes during training or in games for sports performance analysis.

Any of the functionality described above as being executed by a specific component of the electronic controller 140 in the electronic tracking device 105 may be performed, in whole or are in part, by one or more components of the server 110. For example, in some embodiments, the electronic controller 140 extracts the body motion data, detects movements of the subject's body, determines attributes of the detected movement, assigns a rating for the motor exercise, and creates a session record for the subject. In other embodiments, the electronic controller 140 extracts and sends the body motion data to the server 110, and the server 110 detects movements of the subject's body, determines attributes of the detected movement, assigns a rating for the motor exercise, and creates a session record for the subject.

Various embodiments and features are set forth in the following claims.

What is claimed is:

1. A system for markerless tracking of a subject performing a motor exercise, comprising:
    an active 3D infrared camera for capturing depth data of a body of the subject during the motor exercise;
    a memory for pre-storing a movement profile including a plurality of benchmarks; and
    an electronic processor configured to
        extract body motion data for the subject's body from the captured depth data, the body motion data including a set of 3D coordinates for a plurality of body joints for each frame of the captured depth data,
        detect movements of the subject's body using the body motion data,
        determine a set of attributes for the detected movements of the subject's body using the body motion data,
        assign a rating for the motor exercise by comparing the set of attributes for the detected movements of the subject's body with the plurality of benchmarks included in the pre-stored movement profile, and
    create a session record for the subject including the body motion data, the set of attributes for the detected movements of the subject's body, and the assigned rating for the motor exercise,
        wherein the set of attributes is a first set of attributes, wherein the electronic processor is further configured to
        retrieve a second set of attributes from the memory, the second set of attributes having been stored in the memory prior to determining the first set of attributes,
        determine a difference between the first set of attributes and the second set of attributes
        determine whether the subject is in an ON functional state or in an OFF functional state based on the determined difference between the first set of attributes and the second set of attributes, and
        add subject state data to the session record for the subject, the subject state data indicating the determined functional state of the subject.

2. The system of claim 1, wherein the set of attributes for the detected movements of the subject's body including at least one selected from a group consisting of speed, distance, and amplitude.

3. The system of claim 1, further comprising an RGB camera for capturing a sequence of color images of the subject performing the motor exercise, wherein the RGB camera is positioned at a predetermined location relative to the location of the active 3D infrared camera, wherein the RGB camera and the active 3D infrared camera have overlapping fields of view of the subject, wherein for each color image in the sequence of color images, the electronic processor is configured to
    calculate 2D coordinates in the color image for each of the plurality of body joints using the body motion data and prior knowledge of the locations and the fields of view of the cameras,
    alter the color image by superimposing a skeleton on the color image, the skeleton including a visual indicator at the calculated 2D coordinates for each of the plurality of body joints of the subject's body, and
    add the altered color image to the session record for the subject.

4. The system of claim 1, wherein a frame rate of the captured depth data is at least thirty frames per second.

5. The system of claim 1, wherein the motor exercise including at least one motor exercise of the unified Parkinson's disease rating scale.

6. The system of claim 1, wherein the rating is a first rating, wherein the system further comprising a user interface, wherein the electronic processor is further configured to
    receive a second rating for the motor exercise via the user interface,
    determine a difference between the first rating for the motor exercise and the second rating for the motor exercise, and
    adjust at least one of the plurality of benchmarks included in the pre-stored movement profile based on the determined difference between the first rating for the motor exercise and the second rating for the motor exercise.

7. The system of claim 1, wherein the electronic processor is further configured to
    extract facial motion data for a face of the subject from the captured depth data, the facial motion data including a set of 3D coordinates for a plurality of facial points for each frame of the captured depth data, and
    add the facial motion data to the session record for the subject.

8. The system of claim 1, wherein the electronic processor is further configured to
    extract facial motion data for a face of the subject from the captured depth data, the facial motion data including a set of 3D coordinates for a plurality of facial points for each frame of the captured depth data,
    determine identification data for the subject based on the facial motion data, and
    add the determined identification data for the subject to the session record for the subject.

9. The system of claim 1, wherein each of the plurality of benchmarks define a set of conditions associated with a mobility level, wherein the electronic processor assigning the rating for the motor exercise by comparing the set of attributes for the detected movements of the subject's body with the plurality of benchmarks included in the pre-stored movement profile including
    selecting a lowest mobility level with at least one condition met by the set of attributes for the detected movements of the subject's body, and
    assigning the rating for the motor exercise to the selected mobility level.

10. A system for markerless tracking of subjects located in a space, comprising:
    an active 3D infrared camera for capturing depth data in the space; and
    an electronic processor configured to
        extract body motion data for a body of a first subject located in the space from the captured depth data, the body motion data including a set of 3D coordinates for a plurality of body joints for each frame of the captured depth data,
        detect movements of the first subject's body using the body motion data,
        determine a set of attributes for the detected movements of the first subject's body using the body motion data, extract facial motion data for a face of the first subject from the captured depth data, the facial motion data including a set of 3D coordinates for a plurality of facial points for each frame of the captured depth data, determine identification data for the first subject using the facial motion data, and create a session record for the first subject including the body motion data, the detected movements of the first subject's body, the set of attributes, and the identification data for the first subject, wherein the electronic processor is further configured to extract second body motion data for a second body of a second subject located in the space from the captured depth data, the second body motion data including a set of 3D coordinates for a second plurality of body joints for each frame of the captured depth data, detect movements of the second subject's body using the second body motion data, determine a second set of attributes for the detected movements of the second subject's body based on the second body motion data, extract second facial motion data for a second face of the second subject face from the captured depth data, the second facial motion data including a set of 3D coordinates for a second plurality of facial points for each frame of the captured depth data, determine identification data for the second subject based on the second facial motion data, and create a second session record for the second subject including the second body motion data, the detected movements of the second subject's body, the second set of attributes, and the identification data for the second subject.

11. The system of claim 10, wherein the set of attributes for the detected movements of the first subject's body including at least one selected from a group consisting of speed, distance, and amplitude.

12. The system of claim 10, further comprising an RGB camera for capturing a sequence of color images of the first subject, wherein the RGB camera is positioned at a predetermined location relative to the location of the active 3D infrared camera, wherein the RGB camera and the active 3D infrared camera have overlapping fields of view of the first subject, wherein for each color image in the sequence of color images, the electronic processor is configured to calculate 2D coordinates in the color image for each of the plurality of body joints using the body motion data and prior knowledge of the locations and the fields of view of the cameras, alter the color image by superimposing a skeleton on the color image, the skeleton including a visual indicator at the calculated 2D coordinates for each of the plurality of body joints, and add the altered color image to the session record for the first subject.

13. The system of claim 10, wherein a frame rate of the captured depth data is at least thirty frames per second.

14. A method for markerless tracking of a subject performing a motor exercise, comprising:

pre-storing a movement profile in a memory, the pre-stored movement profile including a plurality of benchmarks;

capturing, with an active 3D infrared camera, depth data of a body of the subject during the motor exercise;

extracting, with an electronic processor, body motion data for the subject's body from the captured depth data, the body motion data including a set of 3D coordinates for a plurality of body joints for each frame of the captured depth data;

detecting, with the electronic processor, movements of the subject's body using the body motion data;

determining, with the electronic processor, a set of attributes for the detected movements of the subject's body using the body motion data;

assigning, with the electronic processor, a rating for the motor exercise by comparing the set of attributes for the detected movements of the subject's body with the plurality of benchmarks included in the pre-stored movement profile; and creating, with the electronic processor, a session record for the subject including the body motion data, the set of attributes for the detected movements of the subject's body, and the assigned rating for the motor exercise, wherein the set of attributes is a first set of attributes, wherein the method further comprising retrieving a second set of attributes from the memory, the second set of attributes having been stored prior to determining the first set of attributes;

determining, with the electronic processor, a difference between the first set of attributes and the second set of attributes;

determining, with the electronic processor, whether the subject is in an ON functional state or in an OFF functional state based on the determined difference between the first set of attributes and the second set of attributes; and adding, with the electronic processor, subject state data to the session record for the subject, the subject state data indicating the determined functional state of the subject.

15. The method of claim 14, wherein the set of attributes for the detected movements of the subject's body including at least one selected from a group consisting of speed, distance, and amplitude.

16. The method of claim 14, wherein the motor exercise including at least one motor exercise of the unified Parkinson's disease rating scale.

17. The method of claim 14, wherein each of the plurality of benchmarks define a set of conditions associated with a mobility level, wherein assigning the rating for the motor exercise by comparing the set of attributes for the detected movements of the subject's body with the plurality of benchmarks included in the pre-stored movement profile including selecting a lowest mobility level with at least one condition met by the set of attributes for the detected movements of the subject's body, and assigning the rating for the motor exercise to the selected mobility level.

* * * * *